United States Patent [19]

Hirayama et al.

[11] Patent Number: 5,128,146
[45] Date of Patent: Jul. 7, 1992

[54] APATITE COATED ARTICLE AND PROCESS FOR PRODUCING THE SAME

[75] Inventors: Yasuhiko Hirayama; Haruko Ikata; Satoshi Ojima, all of Tokyo, Japan

[73] Assignee: Asahi Kogaku Kogyo K.K., Tokyo, Japan

[21] Appl. No.: 790,082

[22] Filed: Nov. 13, 1991

Related U.S. Application Data

[63] Continuation of Ser. No. 715,695, Jun. 17, 1991, abandoned, which is a continuation of Ser. No. 287,433, Dec. 21, 1988, abandoned.

[30] Foreign Application Priority Data

Dec. 21, 1987 [JP] Japan .................. 62-323504
Apr. 12, 1988 [JP] Japan .................. 63-89528

[51] Int. Cl.$^5$ .............. A61F 2/28; A61K 9/14
[52] U.S. Cl. .................. 424/484; 424/422; 424/423; 623/16; 623/901
[58] Field of Search .......... 424/422, 423, 484; 623/16, 901

[56] References Cited

U.S. PATENT DOCUMENTS

| | | | |
|---|---|---|---|
| 3,839,618 | 10/1974 | Muehlberger | 219/121 P |
| 4,610,692 | 9/1986 | Eitenmuller | 424/423 |
| 4,869,906 | 9/1989 | Dingeldein et al. | 424/423 |

FOREIGN PATENT DOCUMENTS

| | | |
|---|---|---|
| 2336913 | 7/1977 | France . |
| 0212929 | 3/1987 | France . |
| 52-82893 | 7/1977 | Japan . |
| 53-28997 | 3/1978 | Japan . |
| 58-12651 | 1/1983 | Japan . |
| 62-34558 | 2/1987 | Japan . |
| 62-34559 | 2/1987 | Japan . |
| 62-34566 | 2/1987 | Japan . |
| 1014383 | 12/1965 | United Kingdom . |
| 2162065 | 1/1986 | United Kingdom . |
| 2184357 | 6/1987 | United Kingdom . |

OTHER PUBLICATIONS

Journal of Biomedical Materials Research, vol. 21, 1375-1381, (1987), Groot et al., "Plasma Sprayed Coatings of Hydroxylapatite".
Inter. Journal of Oral & Maxillofacial Implants, vol. 2, No. 2, (1987), Block et al., "Hemimaxillectomy Prosthesis Stabilization of Hydroxylapetite Coated Inplants".
Journal of American Chemical Society, 89:22, Oct. 25, 1967, Bett et al., "Hydroxyepatite Catalysts".

Primary Examiner—Thurman K. Page
Assistant Examiner—C. Azpuru
Attorney, Agent, or Firm—Sughrue, Mion, Zinn, Macpeak & Seas

[57] ABSTRACT

An apatite coated article comprising a substrate having thereon an apatite layer which is formed by flame spraying apatite powder at from about 2,000° to 4,000° C., and a process for producing such an apatite coated article.

7 Claims, 1 Drawing Sheet

APATITE COATED ARTICLE AND PROCESS FOR PRODUCING THE SAME

This is a continuation of application Ser. No. 07/715,695 filed on Jun. 17, 1991 now abandoned, which is a continuation of application Ser. No. 07/287,433 filed on Dec. 21, 1988 (now abandoned) of Yasuhiko HIRAYAMA, Haruko IKATA, and Satoshi OJIMA.

FIELD OF THE INVENTION

The present invention relates to an apatite coated article, and more particularly it relates to an apatite coated article suitable for biomaterials such as artificial teeth, artificial bones, etc.

BACKGROUND OF THE INVENTION

Apatite compounds, particularly hydroxyapatite, have excellent biological affinity because of their similarity to the inorganic component constituting bones and teeth of living organisms. Taking advantage of their biological affinity, they have been utilized as artificial implant ceramics for living organisms in structure such as artificial tooth roots, artificial bones, artificial joints, etc. However, because apatite such as hydroxyapatite is inferior in mechanical strength in comparison to living bones, it cannot be utilized as a member on which a high load is borne.

Various approaches have been investigated for incorporating apatite into a composite material with metals or high-strength ceramics (as disclosed in *The International Journal of Oral & Maxillofacial Implants*, vol, 2, 111 (1987)). Among various methods for producing such a composite material, a thermal spraying method has been intensely investigated in view of the uniformity of adhesion strength and the affinity of the composite with living organisms.

As a thermal spraying method for ceramics, methods utilizing plasma as a heat source have been generally employed. It has been studied in this field of art that apatite is thermal-sprayed using a plasma as a heat source (as disclosed, e.g., in JP-A-62-34558, JP-A-62-34559, JP-A-62-34566, JP-A-53-28997, JP-A-52-82893 and *Journal of Biomedical Materials Research*, vol. 21, 1375 (1987)). However, since apatite suffers from high temperatures of 10,000° C. or more during plasma spraying, undesirable decomposition products such as tricalcium phosphate and calcium oxide are often formed in the final products, and/or sufficient adhesion strength cannot be obtained even though maintaining of adhesion of the thus-formed apatite layer is highly required.

The use of a flame spraying method to alumina is disclosed in JP-A-58-12651, but the flame spraying of apatite has not yet been established.

SUMMARY OF THE INVENTION

An object of the present invention is to provide a process for producing a composite article, and a composite article having an apatite layer which contains no decomposition product formed during the coating process, and wherein the apatite layer has excellent adhesive properties to the substrate comprised of metals, high-strength ceramics, etc.

Other objects and effects of the present invention will be apparent from the following description.

The above objects of the present invention have been attained by an apatite coated article comprising a substrate having thereon an apatite layer which is formed by thermal spraying apatite powder at from about 2,000 to 4,000° C.

DETAILED DESCRIPTION OF THE INVENTION

Figure 1:
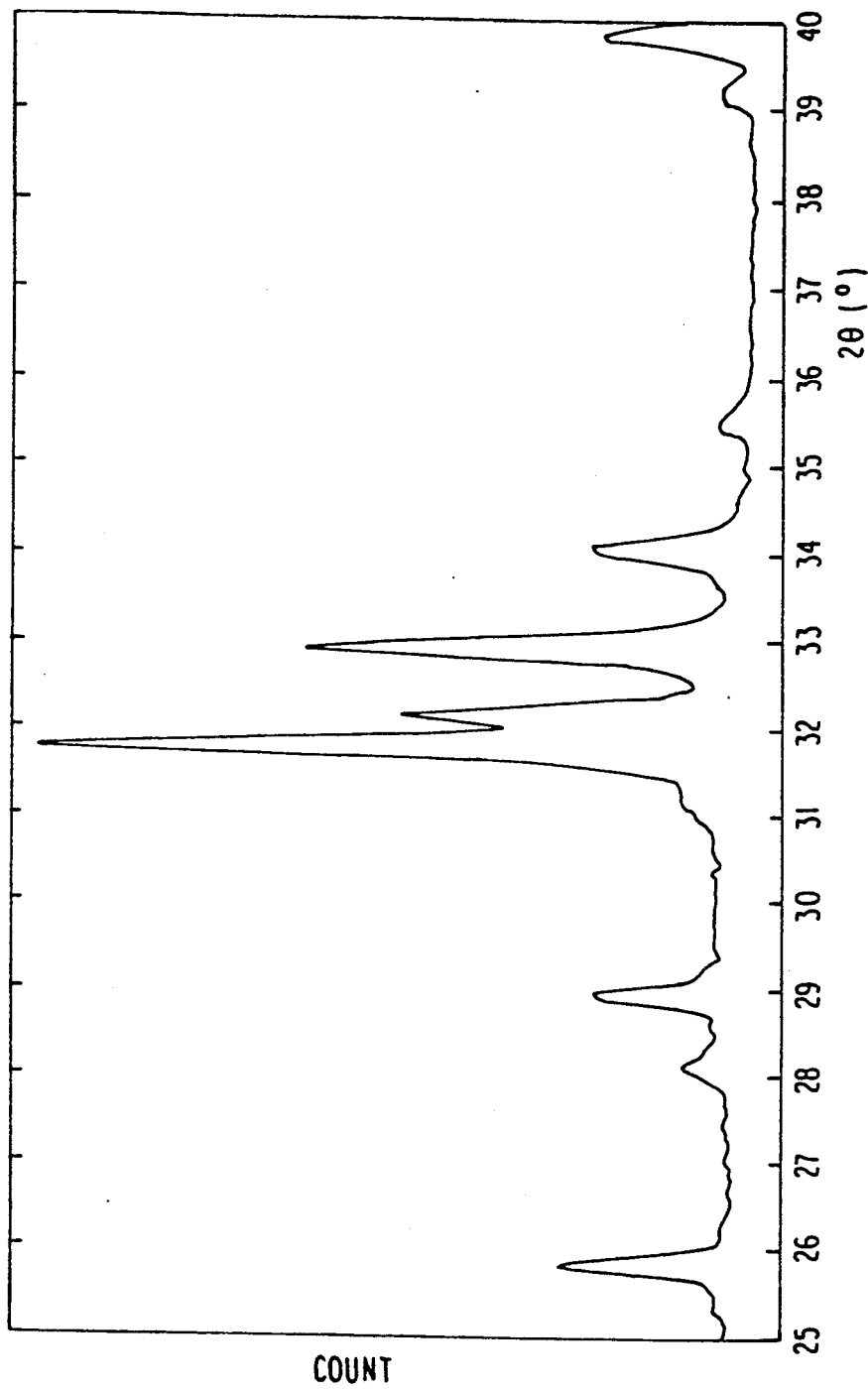
FIG. 1 shows a result of X-ray diffractiometry of the apatite layer provided in Example 1.

The apatite powder used in the present invention preferably has an average particle diameter of from 10 to 30 μm. If the particle diameter is too small, the flowability of the powder is deteriorated, and if the particle diameter is too large, the individual particles do not melt completely during flame spraying. Thus, the above average particle diameter range is preferred, but particles having an average diameter of more than 30 μm can be used if at least the surface of the particles melts upon flame spraying. Particles of the apatite powder preferably have a spherial shape.

The apatite powder used in the present invention can be prepared by any known methods. For example, hydroxyapatite powder can be prepared by the wet method well known in the art in which an aqueous solution of phosphoric acid and a dispersion of calcium hydroxide are mixed to form a precipitate, and the precipitate is granulated by filtering, centrifugation, spray drying, etc., followed by segregating the particles into the above-mentioned diameter range.

The apatite layer of the apatite coated article of the present invention is preferably a hydroxyapatite layer, but it may not be pure hydroxyapatite and may include those in which the hydroxyl groups are substituted by fluorine or chlorine atoms and those in which the calcium atoms are substituted by other metallic atoms. Further, the apatite layer may contain other ceramics such as $Al_2O_3$, $TiO_2$, etc., for adjustment of the thermal expansion coefficient relative to the substrate, improvement in adhesive properties to the substrate, improvement in the strength of the layer, and the like.

The substrate used in the apatite coated material of the present invention is not particularly limited but is preferably selected to have high strength, and maybe selected from metals such as titanium, tantalum, stainless steels, titanium alloys, etc., and high-strength ceramics such as $ZrO_2$, $Al_2O_3$, etc., as well as a cermet. The substrate is preferably blasted before thermal spraying to form unevenness on the surface having a depth of several tens micrometers.

In the present invention, the substrate is shaped to a desired form such as an artificial tooth, an artificial tooth root, an artificial bone, an artificial joint, etc., and then the apatite layer is coated by the thermal spraying method according to the present invention.

The atmospheric temperature to which the apatite particles are exposed during thermal spraying must be from about 2,000° to 4,000° C., and preferably from about 2,500° to 3,000° C. Within these temperature ranges, the decomposition of the apatite is extremely small and a substantially pure apatite layer without decomposition products can be obtained. Thus, a treatment for restoring hydroxyapatite is not required.

As the method for thermal spraying used in the present invention, any method which can attain the above-described temperature range may employed. However, the flame spraying method (as described, e.g., in JP-A-58-12651) can be preferably employed in the present invention.

In the flame spraying method, the atmospheric temperature (i.e., the flame temperature) to which the apatite particles are exposed depends on the composition of a gas used as a heat source, and a mixed gas of oxygen and an inflammable material such as propylene and acetylene is preferably used as a heat source.

In the present invention, it is more preferred to employ a high-speed flame spraying method in which the gas jet speed is a mach number of 2 or more, more preferably a Mach number of 3 or more. By hightening the gas jet speed to such a high speed, a flame having a high energy density can be obtained, and uniformity of the flame sprayed layer and improvement in the adhesive strength can be achieved.

The thickness of the apatite layer of the present invention is not particularly limited and may be any thickness employed in this field of art.

The apatite layer thus coated by the thermal spraying process according to the present invention demonstrates excellent adhesive properties to metals, alloys and high-strength ceramics. For example, when the apatite layer is formed on a blasted surface of a pure titanium material, the adhesive strength between the substrate and the apatite layer is from 100 to 350 kg/cm$^2$ for an apatite layer thickness of from 250 to 350 μm. If the apatite layer thickness is made thinner, higher adhesive strengths can be attained.

The apatite coated article of the present invention is advantageously used as a biomaterial such as an artificial tooth, an artificial tooth root, an artificial bone, an artificial joint, etc., as well as a material for electronics.

The present invention will be described in more detail by referring to the following examples, but is not construed as being limited thereto. Unless otherwise indicated, all parts, ratios, percents, etc. are by weight.

EXAMPLE 1

An aqueous solution of phosphoric acid and a dispersion of calcium hydroxide were reacted by a conventional method (as disclosed in *J. Am. Chem. Soc.*, vol. 88, 5535 (1967)) and the precipitate was granulated by spray drying to obtain hydroxyapatite powder. The hydroxyapatite powder thus-obtained was heat-treated at 1,200° C. and classified to a diameter range of from 10 to 44 μm to have an average particle diameter of 20 μm. The spherical hydroxyapatite powder obtained was flame sprayed on a dental stick made of titanium to a thickness of 200 μm by using a flame spraying device (Model Jet Kote II made by Cabot Co., Ltd.). The result of X-ray diffractiometry of the apatite layer obtained is shown in FIG. 1.

Figure 2:
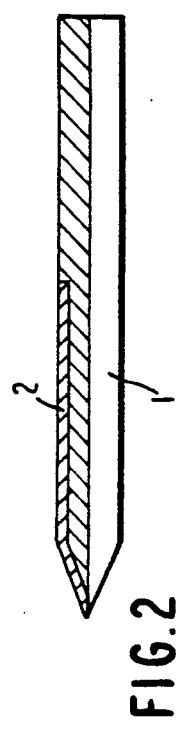
FIG. 2 shows a side view of the dental stick provided in Example 1 in which the upper half of the stick is a cross section.

The thus-obtained apatite coated dental stick is shown in FIG. 2 which is a side view of the stick of which upper half is a cross section. On the part of the dental stick 1 which will be in contact with gingiva, a tooth root, or a mandibular bone after implanting, an apatite layer 2 is provided.

The thus-provided apatite layer was excellent in adhesive properties and bioaffinity, and thus the dental stick obtained could be employed suitably in dental surgery.

EXAMPLE 2

The adhesive strength of the apatite layer according to the present invention was measured pursuant to JIS-H8666. The term "JIS" used herein means "Japanese Industrial Standard". The same spherical hydroxyapatite powder as in Example 1 was flame sprayed onto the blasted surface of a pure titanium rod having a diameter of 25 mm and a length of 40 mm. The flame spraying was conducted at a propylene flow rate of 70 psi and an oxygen flow rate of 90 psi. The crosshead speed upon measuring the adhesive strength was 1 mm/min. As a result of the measurement, the adhesive strength was 224.4 kgf/cm$^2$ for the thickness of the apatite layer of 330.13 μm.

Although only a dental stick is exemplified herein, the present invention is not construed as being limited thereto but can be applied to the making of various materials such as biomaterials including artificial tooth roots and the like by the procedures similar to the above.

As stated in the foregoing, because the apatite layer of the apatite coated article of the present invention is provided by a flame spraying method, the apatite layer is coated at a relatively low temperature, and thus the amount of decomposition products formed during the coating process is extremely small.

Therefore, the present invention can provide an article having an apatite layer which is excellent in adhesive properties to a substrate such as metals, alloys, high-strength ceramics, etc., and bioaffinity, and has a high uniformity and a high strength. The apatite coating process of the present invention can be applied advantageously to produce artificial tooth roots, dental sticks, artificial bones, artificial joints, etc.

While the invention has been described in detail and with reference to specific examples thereof, it will be apparent to one skilled in the art that various changes and modifications can be made therein without departing from the spirit and scope thereof.

What is claimed is:

1. A process for producing an apatite coated article comprising a substrate having thereon an apatite layer, said process comprising flame spraying apatite powder at from about 2,000° to 4,000° C. onto said substrate, wherein said flame spraying is high-speed flame spraying using a gas jet wherein the gas jet speed has a Mach number of 2 or more.

2. A process as claimed in claim 1 wherein said apatite powder has an average particle diameter of from 10 to 30 μm.

3. A process as claimed in claim 1, wherein said apatite powder is hydroxyapatite powder.

4. A process as claimed in claim 1, wherein said substrate is selected from a metal, an alloy and high-strength ceramics.

5. A process as claimed in claim 1, wherein said flame spraying is conducted at a temperature of from about 2,500° to 3,000° C.

6. A process as claimed in claim 1, wherein wherein the gas jet speed has a Mach number of 3 or more.

7. A process as claimed in claim 1, wherein the decomposition of the apatite is small and a substantially pure apatite layer is obtained without decomposition products being present.

* * * * *